United States Patent [19]

Gibson et al.

[11] 4,140,580
[45] Feb. 20, 1979

[54] BROTH FOR INDICATING PRESENCE OF CANDIDA YEAST AND OTHER YEASTS AND FUNGI

[75] Inventors: Sandra F. Gibson, Chesterfield, Mo.; Michael C. Meyer, O'Fallon, Ill.

[73] Assignee: McDonnell Douglas Corporation, St. Louis, Mo.

[21] Appl. No.: 749,249

[22] Filed: Dec. 10, 1976

Related U.S. Application Data

[63] Continuation-in-part of Ser. No. 682,660, May 3, 1976, abandoned.

[51] Int. Cl.² ............................................. C12K 1/06
[52] U.S. Cl. .................................... 195/100; 195/102
[58] Field of Search ................ 195/99, 100, 101, 101, 195/102, 103

[56] References Cited

PUBLICATIONS

W. R. Bailey and E. G. Scott; Diagnostic Microbiology, 2nd Ed., the C. V. Mosky Company; 1966; pp. 26, 295 and 296.

*Primary Examiner*—Raymond N. Jones
*Assistant Examiner*—Robert J. Warden
*Attorney, Agent, or Firm*—Gravely, Lieder & Woodruff

[57] ABSTRACT

A broth medium for the detection of Candida yeasts, *Saccharamyces cerevisiae, Torulopsis glabrata*, and *Aspergillus niger* in urine. The medium employs chloramphenicol and potassium tellurite to inhibit the growth of gram-positive and gram-negative organisms. The medium also uses reduced aniline blue biological pH indicator.

4 Claims, No Drawings

BROTH FOR INDICATING PRESENCE OF CANDIDA YEAST AND OTHER YEASTS AND FUNGI

REFERENCE TO PRIOR APPLICATIONS

This application is a continuation-in-part of copending application Ser. No. 682,660, filed May 3, 1976 now abandoned, entitled BROTH FOR INDICATING PRESENCE OF CANDIDA YEAST AND OTHER FUNGI.

BACKGROUND OF THE INVENTION

Candida yeasts, *Saccharamyces cerevisiae, Torulopsis glabrata,* and *Aspergillus niger* are fungi which occur in urine. The presence of these microorganisms in urine is a reliable indicator of urinary tract, throat, skin, etc., infection. If any of these organisms are present in a given sample of urine, it is also possible that other bacterial infection is present.

The medium of this invention is an improved medium designed for use with the optical detection system disclosed in U.S. applications Ser. Nos. 255,533 filed May 22, 1972 now U.S. Pat. No. 3,904,677 and 461,249 filed Apr. 16, 1976 now U.S. Pat. No. 3,963,355 in the improved devices disclosed and claimed in applications filed on May 3, 1976 by Charles, Jones, Staples and Wiegner Ser. No. 682,664 now U.S. Pat. No. 4,118,280 entitled AUTOMATED MICROBIAL ANALYZER and Ser. No. 682,728 now U.S. Pat. No. 4,116,775 entitled MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic acitivity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

We have discovered a medium which can selectively identify Candida yeasts and other yeasts and fungi in urine when the medium is placed in the wells of the cards described in application AUTOMATED MICROBIAL ANALYZER.

Positive results are indicated by means of a change in color of a pH indicator solution incorporated into the medium which causes a change in the light transmitting character of the medium, which change is read by the mechanism described in application AUTOMATED MICROBIAL ANALYZER. The entire test can be completed within 12-18 hours, whereas current methods of detection require from about 36 to about 48 hours.

SUMMARY OF THE INVENTION

This invention involves a broth medium for the detection of *Candida* yeasts, *Saccharamyces cerevisiae, Torulopsis glabrata,* and *Aspergillus niger* in urine.

The medium contains Phytone Peptone, dextrose, chloramphenicol, potassium tellurite, and a biological pH indicator.

The novelty of the invention lies in the incorporation into a medium of chloramphenicol, which operates to inhibit the growth of gram-positive and gram-negative organisms, and reduced aniline blue, which allows use of the medium in the AUTOMATED MICROBIAL ANALYZER, by means of which the presence of *Candida* yeasts and other yeasts and fungi are detected by color change in the medium.

DETAILED DESCRIPTION

The specific yeasts which have been detected by the broth of this invention include *Candida albicans, Candida stellatoides, Candida tropicalis, Candida parapsilosis, Candida krusel, Candida pseudotropicalis, Candida guillermondii, Saccharamyces cerevisiae,* and *Torulopsis glabrata.* In addition the fungus *Aspergillus niger* also have been detected by the broth of this invention.

The detection broth of the present invention contains from 18 to 22 gm/l nutrients, about 19 to about 21 ml/l of an indicator which indicates the positive growth of the aforementioned yeasts and fungi, about 0.97 to about 1.03 gm/l chloramphenicol and about 2.9 to about 3.1 ml/l potassium tellurite (1% stock solution), which operate as biological inhibitors to inhibit the growth of gram-positive and gram-negative organisms which normally give positive results in tests for yeast or fungi, and about 1.8 to about 2.2 gm/l of sodium thioglycollate.

The nutrient portion of the medium contains from about 9 to about 11 gm/l dextrose, and from about 9 to about 11 gm/l Phytone Peptone from BBL.

Phytone Peptone is a papaic digest of soya meal and has a high vitamin content, especially thiamine. Any suitable peptone, such as Thiotone from BBL and Proteose Peptone #3 from Difco can be substituted for Phytone.

The purpose of the dextrose is to provide a substrate for yeast fermentation. A positive reaction from action of yeast on the sugar will result in production of acid.

A suitable biological pH indicator is reduced aniline blue. This indicator is used because it will turn from colorless to blue, at a pH of 6.8 and less as the medium becomes acid thus changing the light transmitting characteristics of the medium, which change is observed and recorded by the mechanism described in application AUTOMATED MICROBIAL ANALYZER.

Sodium hydroxide is used to adjust the initial pH of the medium to 6.9. The medium must be held at about a neutral pH because acid will impair the sensitivity of the reduced aniline blue indicator. As the yeast ferments the sugar, acid is produced which causes the pH of the medium to go down and institutes the color change in the aniline blue indicator which goes from about colorless to blue as more acid enters the system.

An important aspect of this invention lies in the action of the chemical inhibitors, chloramphenicol, and potassium tellurite. These inhibitors act to inhibit the growth of organisms other than yeast and fungi.

Growth of species of gram-positive and gram-negative organisms which result in high yields of positives by conventional detection methods is inhibited by these chemical inhibitors in the process.

The concentration of chloramphenicol can be from about 0.97 to about 1.02 gm/l, and it is most effective at 1.0 gm/l.

The concentration of potassium tellurite (1% stock solution) can be from about 2.9 to about 3.1 ml/l, and it is most effective at 3.0 ml/l. If the concentration of any inhibitor is too low, a higher yield of unwanted false positives occurs. If the concentration is too high, a lower yield of positives occurs.

EXAMPLE I

To prepare a yeast detection broth of a 2X strength in an amount of 100 ml, the following components are thoroughly mixed in the specified amounts:

| Distilled Water | 96 | ml |
| --- | --- | --- |
| Phytone | 2.0 | gm |
| Dextrose | 2.0 | gm |
| Chloramphenicol | 0.16 | gm |
| Potassium Tellurite (1% Stock Solution) | 0.6 | ml |

The pH of the mixture is adjusted to 6.2. 4.0 ml of reduced aniline blue indicator is added. The pH of the mixture should be adjusted to 6.9, acid should not be added. Base may be added if necessary. 0.4 gm of sodium thioglycollate from Nutritional Biochemical Company is added, and the mixture is filter sterilized.

The medium is at double (2X) the usual concentration for use in the wells and card described in application entitled AUTOMATED MICROBIAL ANALYZER.

The reduced aniline blue indicator is made by the process described in Aldridge and Meyer application for U.S. patent Ser. No. 682,652 entitled "Sensitive pH Indicator" filed May 3, 1976 now U.S. Pat. No. 4,062,876.

What is claimed is:

1. A broth medium for detection of *Candida* yeasts, *Saccharamyces cerevisiae*, *Torulopsis glabrata*, and *Aspergillus niger* comprising:
   (a) a nitrogen source,
   (b) a carbon source,
   (c) chloramphenicol and potassium tellurite to inhibit growth of gram-positive and gram-negative organisms, and
   (d) a biological pH indicator which changes color as the medium becomes more acidic from metabolic activity of the organism.

2. The medium of claim 1 wherein about 0.97 to about 1.03 gm/l chloramphenicol and about 2.9 to about 3.1 ml/l potassium tellurite (1% stock solution) is used.

3. The medium of claim 1 comprising per liter of medium:
   (a) about 9 to about 11 gm Phytone Peptone,
   (b) about 9 to about 11 gm dextrose,
   (c) about 1.8 to about 2.2 gm sodium thioglycollate,
   (d) about 0.97 to about 1.03 gm chloramphenicol,
   (e) about 2.9 to about 3.1 ml potassium tellurite (1% stock solution),
   (f) about 19 to about 21 ml reduced aniline blue,
   (g) the medium having a pH of about 6.9.

4. The medium of claim 1 comprising per liter of medium:
   (a) 10 gm Phytone Peptone,
   (b) 10 gm dextrose,
   (c) 2 gm sodium thioglycollate,
   (d) 1 gm chloramphenicol,
   (e) 3 ml of 1% stock solution of potassium tellurite, and
   (f) 20 ml reduced aniline blue,
   (g) the medium having a pH of 6.9.

* * * * *